United States Patent
Phillips (10) Patent No.: US 11,439,537 B2
(45) Date of Patent: Sep. 13, 2022

(54) OPTHALMIC CANNULATED WOUND-STABILIZING BLADE AND METHOD OF USING SAME

(71) Applicant: Paul Phillips, Sewickley, PA (US)

(72) Inventor: Paul Phillips, Sewickley, PA (US)

( * ) Notice: Subject to any disclaimer, the term of this patent is extended or adjusted under 35 U.S.C. 154(b) by 72 days.

(21) Appl. No.: 16/845,864

(22) Filed: Apr. 10, 2020

(65) Prior Publication Data
US 2021/0315738 A1  Oct. 14, 2021

(51) Int. Cl.
*A61F 9/013* (2006.01)
*A61F 9/00* (2006.01)
*A61F 9/007* (2006.01)

(52) U.S. Cl.
CPC .......... *A61F 9/0133* (2013.01); *A61F 9/0008* (2013.01); *A61F 9/00781* (2013.01)

(58) Field of Classification Search
CPC .... A61F 9/0133; A61F 9/0008; A61F 9/0017; A61F 9/007; A61F 9/00736; A61F 9/00754; A61F 9/00781; A61B 17/3211
See application file for complete search history.

(56) References Cited

U.S. PATENT DOCUMENTS

| | | |
|---|---|---|
| 2,989,053 A | 6/1961 | Hamilton |
| 4,642,090 A | 2/1987 | Utrata |
| 5,224,950 A * | 7/1993 | Prywes ................. A61F 9/0133 606/166 |
| 5,792,099 A | 8/1998 | Decamp et al. |
| 5,800,406 A | 9/1998 | Kritzinger et al. |
| 5,938,632 A | 8/1999 | Ellis |

(Continued)

FOREIGN PATENT DOCUMENTS

| | | |
|---|---|---|
| EP | 1809219 B1 | 3/2009 |
| EP | 3 530 304 A1 | 8/2019 |

(Continued)

OTHER PUBLICATIONS

Notification of Transmittal of the International Search Report (Forms PCT/ISA/220 and PCT/ISA/210) and the Written Opinion of the International Searching Authority (Form PCT/ISA/237) dated Aug. 17, 2021, by the ISA/US, Commissioner for Patents in corresponding International Application No. PCT/US21/25373. (16 pages).

*Primary Examiner* — Diane D Yabut
*Assistant Examiner* — Brigid K Byrd
(74) *Attorney, Agent, or Firm* — Buchanan Ingersoll & Rooney PC (57) ABSTRACT

A surgical cannulated blade instrument includes a blade portion having a pointed end, a top surface, and a bottom surface opposite the top surface, an increasing diameter portion having a diameter which increases in a direction away from the pointed end, and a cannula portion having a lumen opening at a location between the pointed end and the increasing diameter portion. An eye surgery method includes incising a cornea of an eye using a blade portion of a surgical cannulated blade instrument to create an opening in the cornea, injecting injectable into an anterior chamber of the eye through the opening by a lumen of the surgical cannulated blade, and stabilizing the eye by engaging an increasing diameter portion of the surgical cannulated blade with the opening.

11 Claims, 8 Drawing Sheets

(56) References Cited

U.S. PATENT DOCUMENTS

| | | | |
|---|---|---|---|
| 6,004,302 A * | 12/1999 | Brierley | A61F 9/00781 |
| | | | 604/523 |
| 6,056,764 A | 5/2000 | Smith | |
| 6,627,620 B1 | 9/2003 | Nielsen | |
| 7,070,583 B1 | 7/2006 | Higuchi et al. | |
| 7,247,160 B2 | 7/2007 | Seiler et al. | |
| 8,455,465 B2 | 6/2013 | Gavard | |
| 10,272,181 B2 | 4/2019 | Gavard Molliard | |
| 2008/0033351 A1 * | 2/2008 | Trogden | A61K 9/0051 |
| | | | 604/57 |
| 2008/0091104 A1 | 4/2008 | Abraham | |
| 2009/0030381 A1 | 1/2009 | Lind et al. | |
| 2012/0083727 A1 | 4/2012 | Barnett | |
| 2013/0172917 A1 | 7/2013 | Saito | |
| 2015/0148729 A1 * | 5/2015 | Pinchuk | A61M 27/002 |
| | | | 604/8 |
| 2017/0216536 A1 | 8/2017 | Scott | |
| 2018/0360661 A1 | 12/2018 | Kahook et al. | |
| 2020/0038008 A1 * | 2/2020 | Depenbusch | A61B 17/0231 |
| 2020/0107961 A1 | 4/2020 | Kahook et al. | |

FOREIGN PATENT DOCUMENTS

| | | |
|---|---|---|
| WO | 2006079766 A1 | 8/2006 |
| WO | 2019200336 A1 | 10/2019 |
| WO | 2021/030873 A1 | 2/2021 |

* cited by examiner

OPTHALMIC CANNULATED WOUND-STABILIZING BLADE AND METHOD OF USING SAME

TECHNICAL FIELD

The present invention relates to a combination ophthalmic cannulated wound-stabilizing blade with a stabilizing shoulder and methods of its use for the treatment of eye diseases, such as cataracts, by minimizing the potential tissue damage and risk of infection while improving time to completion of the surgery. The combination blade and cannula can be used for simultaneous cutting of tissue and delivery of compounds to the eye followed by stabilization of the eye during further steps of the procedures. The present invention also relates to a novel surgical technique for administering an anesthetic and viscoelastic mixture to the anterior chamber of the eye using the proposed cannulated wound-stabilizing blade.

BACKGROUND

A number of surgeries are currently performed that require access to the anterior chamber of the eye. In each case the administration of anesthetic and a viscoelastic compound are crucial for patient comfort and maintenance of eye structure and integrity during surgery. Non-exhaustive examples of these surgeries include cataract and lens replacement surgeries, corneal transplants, vitreo retinal surgeries, vitreous injections and implantation procedures, and glaucoma surgery.

Deficiencies in the prior art currently expose patients to a number of complications when receiving eye surgery. For example, it is important to create an incision through the cornea that will result in proper healing and rehabilitation of the wound. It is desirable, when making such an incision, to avoid deformation of the eye tissues and to prevent inadvertent tearing or widening of the incision which can be caused by a lack of tissue stability and rigidity, leading to wound integrity issues. Further, during any surgery it is critical to reduce both the number of tools and the frequency of objects inserted into an incision to mitigate the risk of infection and decreases surgical time.

Cataracts result from clouding of the eye's natural crystalline lens due to, among other causes, aging, injury and some genetic disorders. They are common as people age with approximately half of people developing cataracts that require treatment before the age of 80. Without corrective surgery cataracts can lead to total loss of vision in the affected eye, which for some people will mean blindness if cataracts form in both eyes. For those without total vision loss it can still mean a reduced quality of life since humans rely so heavily on their eyesight to navigate the world. Luckily, cataract surgery is an outpatient procedure usually lasting less than half an hour.

In cataract surgery a surgeon will first prepare a preservative-free anesthetic containing syringe, and a viscoelastic syringe kit. Additionally, a paracentesis blade, a microkeratome blade and an additional instrument or device to stabilize the eye is required. The surgeon will begin by placing a paracentesis incision in the cornea at the limbus of the eye followed by injection of anesthetic. Next, the surgeon injects the viscoelastic compound followed by the creation of a second, larger, "main," incision into the cornea at the limbus with a microkeratome blade. During the placement of the second incision, most surgeons will require an additional instrument to stabilize the eye. Now the surgeon will work to emulsify the clouded lens and remove it from the eye, replacing it with a clear synthetic lens. It is important to note that each step involves removal of the previous tool and insertion of the next through the same incision.

Current deficiencies in cataract surgery arise from the serial nature of these steps. The insertion of multiple objects into the eye increases the possibility of infection. The surgeon must also take time to switch between tools during the surgery, increasing the amount of time the surgery takes as well as increasing the possibility of mistakes. The second incision is more difficult to make owing to its size, the loss of fluid from the eye, and a subsequent decrease in firmness of the eye. Further, the eyelid is held open during the surgery but the eye itself is still free to move around adding to the difficulty in properly placing the second incision. The lack of stability when making the second incision increases the chance of unintentional tissue injury or irreversible damage to the eye. The amount of time the operation takes must also be taken into consideration. Patients are conscious during the procedure and any reduction in the time the surgery takes can decrease the stress and discomfort on the patient and increase the efficiency of the surgeon, which decreases the chances of patient movement and resulting complications.

SUMMARY

The present disclosure proposes to simplify ophthalmic surgery by combining techniques of the surgery and coupling it with a novel ophthalmic cannulated blade. The present disclosure combines the viscoelastic and anesthetic prior to surgery by vacating an approximately 0.2-0.5 mL space in the viscoelastic syringe. This space is then filled with lidocaine or other appropriate anesthetic. A cannula is then primed with lidocaine and securely affixed to the end of the viscoelastic syringe. This combination allows the surgeon to inject lidocaine and viscoelastic after making the first incision with one continuous depression of the syringe plunger instead of inserting and removing two syringes from the eye.

The present disclosure further proposes combining the blade and cannula in a novel way so as to minimize the steps being performed. A paracentesis blade with an opening and hollow shaft for attachment to a syringe is proposed. This will allow a surgeon to make the first incision, inject lidocaine and inject viscoelastic all in one step. This combinatorial blade will be outfitted with an eye stabilizing shoulder that, after injection of viscoelastic, will allow the apparatus to be inserted further into the incision to stabilize and hold the eye for the subsequent incision.

The proposed method solves the deficiencies in current ophthalmic operations by combining three surgical steps into one and improving upon the current surgery by innovatively providing a new way to stabilize the eye. The numerous benefits include reducing risk of postoperative infection, minimizing patient discomfort, and minimizing the risk of dangerous mistakes by the surgeon. The method also has the added benefit of saving the surgeon time. Further, the eye stabilizing wing introduces a new technique to reduce the risk of loss of control and misplaced incisions or injury to the patient due to eye movements and tissue instability.

Examples of bladed cannulas are disclosed in US 2012/0083727A1, US 2017/0216536A1, US 2009/0030381A1, U.S. Pat. No. 7,070,583 B1 and ophthalmic knives are disclosed in US 2013/0172917 A1, U.S. Pat. Nos. 6,056,764, 4,642,090. These bladed cannulas differ from the present disclosure because they are not used to create surgical incisions, but rather to create minimally invasive self-sealing puncture wounds. These ophthalmic surgical knives do not currently incorporate a cannula directly into the blade for injection of materials into the eye after incision. Further, they lack the eye stabilizing should or wing that is critical for the function and use of the present disclosure. The present disclosure distinguishes itself from these bladed cannulas by being designed to create an incision, followed by injection of material directly into the anterior chamber of the eye, and by providing stabilization of the eye for further incisions to be made.

DETAILED DESCRIPTION

The present disclosure relates to a surgical instruments and methods of using it for the treatment of various conditions including eye diseases, such as cataracts. This ophthalmic cannulated wound-stabilizing blade can be used for cutting the tissues of the eye, for example, by making an incision in the cornea at the limbus or through sclera, depending on the desired location of the incision. Further this cannulated wound-stabilizing blade also allows for the injection of compounds directly into the incision. For example, a syringe sequentially loaded with lidocaine and a viscoelastic compound is used to deliver these compounds to the eye through the cannulated wound-stabilizing blade. This disclosure also relates to a device for stabilizing tissues after making an incision, for example, holding an eye in place for a second incision during cataract surgery. This disclosure also relates to surgical techniques. For example, the present application discloses a method of preparing viscoelastic in combination with lidocaine to be delivered through a hollow surgical cannulated wound-stabilizing blade so as to minimize the steps required in surgery.

Figure 1:
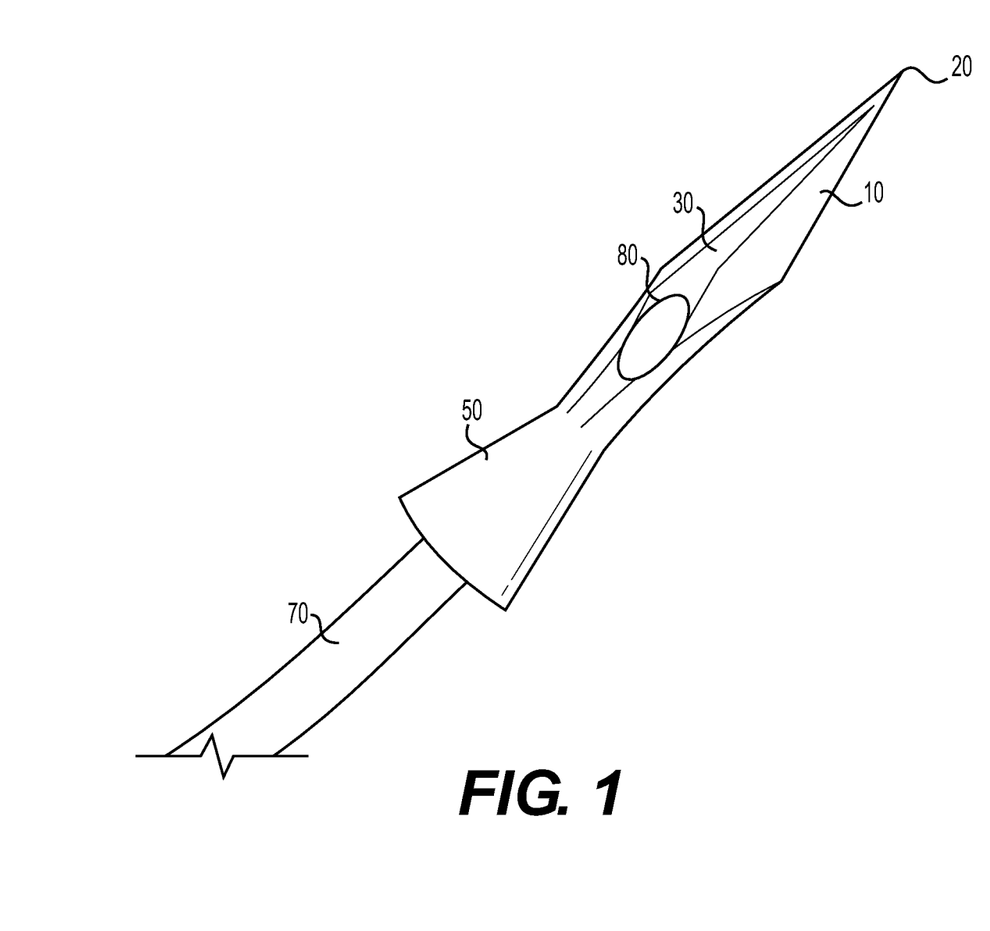
FIG. 1 illustrates a partial plan view of a surgical cannulated blade according to an embodiment of the present application.
Figure 2:
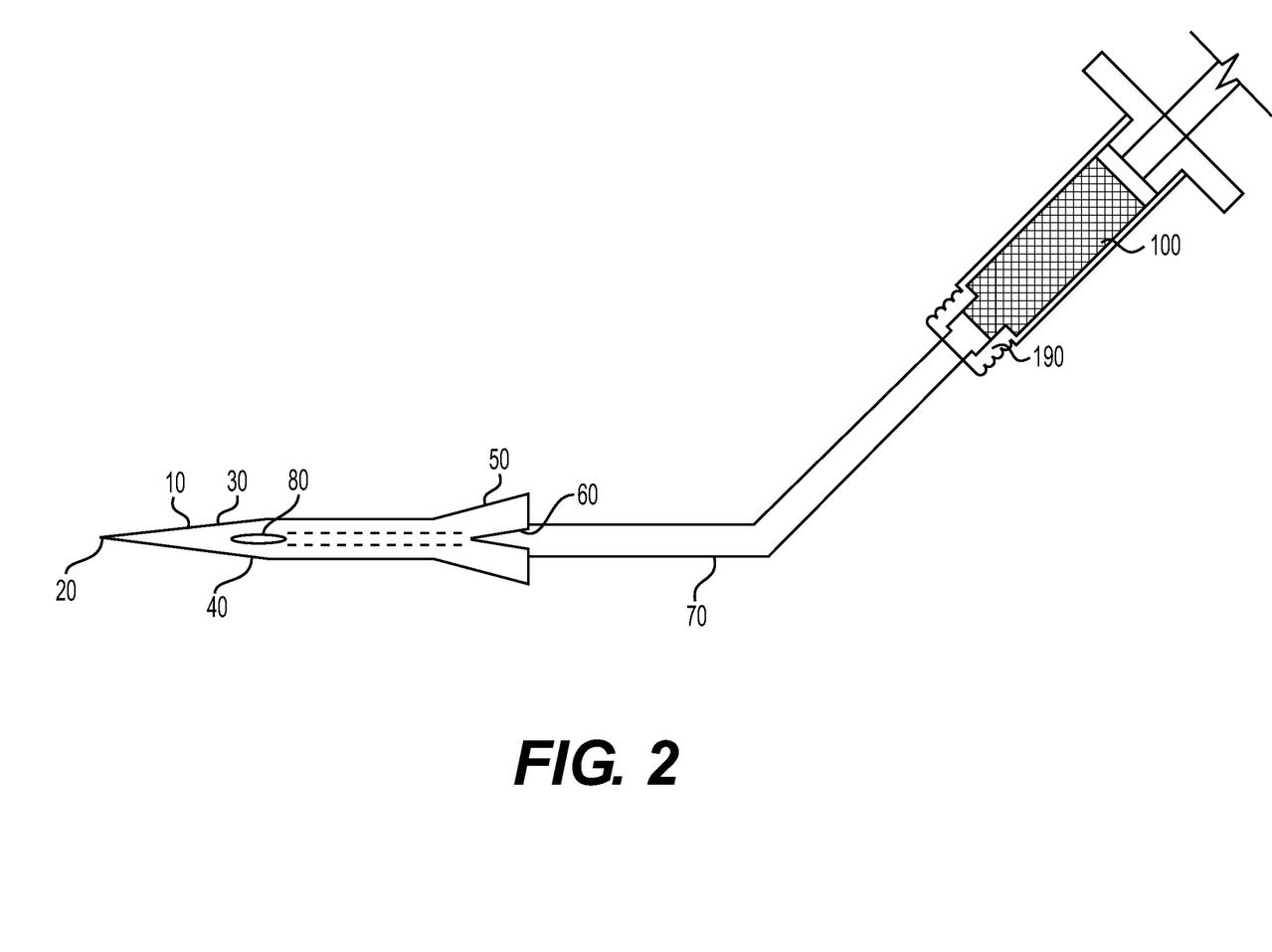
FIG. 2 illustrates a side view of the surgical cannulated blade according to an embodiment.

In the embodiments illustrated in FIGS. 1 and 2, a surgical cannulated blade instrument includes a blade portion 10 having a pointed end 20, a top surface 30, and a bottom surface 40 opposite the top surface 30, an increasing diameter portion 50 having a diameter which increases in a direction away from the pointed end 20, and a cannula portion 70 having a lumen 80 opening at the top surface 30 of the blade portion 10 at a location between the pointed end 20 and the increasing diameter portion 50. The increasing diameter portion 50 functions as a shoulder, as discussed in more detail below. In the embodiment, the blade portion 10 is upwardly curved to at least partially surround the cannula portion 70. However, the lumen 80 can instead open at the bottom surface 40 of the blade portion 10, or between the blade portion 10 and the increasing diameter portion 50, again, on either on the top or bottom side of the cannula portion 70. Furthermore, the blade portion 10 can be formed simply as a widening of the cannula portion 70 rather than a separate element mounted to the cannula portion 70. The shape of the blade portion 10 can vary, as evident from FIGS. 1 and 2, without departing from the spirit and scope of the invention.

Furthermore, there is at least one indent 60 in the increasing diameter portion 50, which acts as an opening in the shoulder, as discussed in more detail below. The end of the cannula portion 70 opposite the blade portion 10 can include a threaded connection 190 for attachment to a syringe 100.

In one embodiment, the disclosure relates to a surgical cannulated wound-stabilizing blade suitable for making incisions and injecting compounds into the formed incision. The blade of said embodiment comprises 4 identical isosceles triangles joined at their long edges such that the base forms a rhombus or square. The edges formed from the acutely angled corners, measured internally, of the pyramidal solid are sharp. The solid forms a continuous piece of material with the shaft of the blade. The protruding corners of the blade are connected to the shaft by continuous material that sweeps back toward the blade shaft forming an approximate diamond or kite shaped cross section of the blade when bisected by a horizontal place.

In other embodiments the material near the tip may comprise 4 identical isosceles joined at their long edges such that the base forms a rhombus or square and such that the edges of the pyramid form a more obtuse angle, measured internally, than the one that would be formed by the pyramid, thus forming a tip with a broader point than would otherwise be present. In some embodiments the tip at the end of the blade is flattened relative to the rest of the blade.

In another embodiment, the flattened blade is roughly rhomboid in shape. Further, the rhomboid that forms the blade may be defined by theoretical lines, drawn between opposite corners, which either intersect perpendicularly or do not intersect perpendicularly. The blade has one sharpened edge used for cutting on the leading edge of the rhomboid that extends beyond the blade handle. In some embodiments the lower two edges of the rhomboid may curve to meet the shaft.

In another embodiment, the blade tapers from the end of the shaft without extending past the maximum width of the shaft. Further the material comprising the shaft slopes at equal angles toward the central plane of the shaft until they meet to form a sharp, wedge shaped tip that is not conical or cylindrical.

In further embodiments, a shaft extends back from the rhombus at the base of the pyramidal blade. A lumen extends the length of the shaft and blade where it terminates with openings at both the blade and the opposite end of the shaft forming a continuous tube the runs the length of the instrument. The shaft may be cylindrical, rectangular or be an elongated piece of material with both corners and rounded edges. Preferably the shaft is used to convey fluids to or from the blade. In one embodiment an upper portion of the shaft may be of a larger diameter than the shaft immediately above the blade. This difference in diameter forms a projection of material at a 90° angle from the shaft extending back from the blade.

In the present embodiments of the disclosure the tip is 0.75-3.5 mm wide. Preferably, the blade is between 0.75 and 1 mm wide. In the present embodiments of the disclosure the blade is not thicker than the diameter of the shoulder, which is described in detail below.

In a preferred embodiment, a material suitable for sterilization and use in surgery is used. Preferably a surgical steel and/or a plastic that will not deform during sterilization is used. In other embodiments, the device could be made from a reusable material such as a diamond blade or titanium.

In a preferred embodiment, the lumen comprises a termination in the blade without disrupting the edge of the blade. Preferably, the opening of the lumen is located on the top or bottom face of the blade, or behind the blade. Preferably the opening is between 14 and 33 gauge. Most preferably the opening is 27 gauge.

In a preferred embodiment the shaft may comprise a bend suitable for holding the blade comfortably in a level position. Preferably the angle is 10°, 15°, 20°, 25°, 30°, 35°, 40°, 45°, 50°, 55°, 60°, 65°, 70°, 75°, 80°, 85°, or 90°. Most preferably the bend is between 41 and 47 degrees. In a further embodiment the shaft may comprise a second bend. Preferably the angle is 10°, 15°, 20°, 25°, 30°, 35°, 40°, 45°, 50°, 55°, 60°, 65°, 70°, 75°, 80°, 85°, or 90°. In other preferred embodiments the shaft is not bent.

In a preferred embodiment the shaft comprises a protruding shoulder behind the blade that is flat or rounded forming a vertical cross-section, defined as perpendicular to the blade shaft, that is rectangular, circular, ellipsoid, semicircular or any geometry defined by flat and/or curved edges with rounded and/or angled corners. Further the shoulder above comprising at least one width that is at least equal to the width of the blade at one or more points. In a related embodiment the shoulder comprises at least one width where the width of the shoulder is wider than the blade. In a yet another embodiment the shoulder comprises at least one width narrower than the blade. In some embodiments the shoulder comprises all three widths. In some embodiments the shoulder is thicker, thinner or the same thickness as the blade. In other embodiments the thickness of the shoulder varies longitudinally as it protrudes away from the blade. In some embodiments the shoulder comprises 0, 1, 2 or more openings extending in the longitudinal direction of the shaft. The openings being sufficient to allow the efflux of fluid around the shoulder. For example, these openings may be drilled openings or channels cut through the shoulder material or notches cut into the surface or sides of the material. In the present embodiment the shoulder extends outward with straight edges from the shaft. In other embodiments the shoulder extends from the shaft along an arc. In still further embodiments the shoulder may extend, in combination, both towards and away from the shaft one or more times, to form ridges, grooves or spaces within the shoulder material. For example, the shoulder may take the form of two spheres bridged by a narrow strip of material or two cones joined end to end.

In another embodiment the blade is absent from the shaft, forming a shaft with a lumen terminating in the blunt shoulder.

In a preferred embodiment one end of the shaft is adapted to fit the end of a standard syringe. The adapted shaft may comprise a set of threads for attachment to a threaded syringe. The adapted shaft may comprise an opening suitable for attachment to a syringe by friction only. In a further embodiment the device will be secured to the syringe by a locking ring. In other embodiments the apparatus may include a hollow handle. The handle may comprise a lumen that extends the length of the handle and forms a continuous space with the lumen of the blade and shaft. In other embodiments the handle is hollow only part of the way and contains a port in the side of the handle that connects to a lumen that is continuous with the lumen of the blade and shaft. The handle is preferably long enough to be handled comfortably by a surgeon, between 20 and 200 mm. In some embodiments the handle contains a textured grip. In some embodiments the handle contains protrusions to keep it from rolling across a flat surface. In some embodiments the handle is made of metal, plastic or a combination of the two. In some embodiments the handle connects to surgical tubing. In other embodiments the handle can connect to a syringe. In other embodiments the handle contains a syringe plunger and the lumen of the handle is filled with a liquid forming one continuous syringe/blade-type instrument.

In a preferred embodiment, the hollow shaft conveys a fluid material or mixture to or from the target tissue following cutting of the target tissue. In a preferred embodiment the fluid to be conveyed is contained in a syringe. In a further embodiment the fluid comprises anesthetic, viscoelastic or a layered formulation of anesthetic and viscoelastic. In a preferred embodiment the anesthetic comprises essentially lidocaine. Another embodiment includes layering the lidocaine and viscoelastic, such that lidocaine will enter the lumen of a cannula prior to the viscoelastic when the compounds are injected. Preferably, 0.2-0.5 ml of lidocaine is added.

In a preferred embodiment, the shoulder is inserted into an opening in a tissue. In a further embodiment the shoulder is used to stabilize an organ or tissue during a procedure. In another embodiment, openings in the shoulder allow fluids to exit the incision while the shoulder is inserted.

In a preferred embodiment, the apparatus is used to perform ophthalmic surgery. In a further embodiment the surgery is cataract surgery, lens replacement surgeries, Descemet's stripping automated endothelial keratoplasty (DSAEK), Descemet's membrane endothelial keratoplasty (DMEK), Descemet's stripping without endothelial keratoplasty (DWEK), corneal transplants, vitreo-retinal surgeries, vitreous injections or implantation procedures or glaucoma surgery. In an exemplary embodiment the surgery is cataract surgery.

In an exemplary embodiment the blade is used to cut the tissues of the eye. Preferably the tissue of the limbus of the cornea. The opening in the blade conveys fluids to be introduced into the eye via a syringe. Preferably the fluid is a layered anesthetic and viscoelastic mixture. Further the anesthetic is lidocaine. The lidocaine of the mixture is layered such that it is injected completely before the addition of the viscoelastic. This layered mixture can be provided by starting with a syringe containing viscoelastic, ejecting some of the viscoelastic from the syringe, and charging lidocaine into the syringe to result in a layer of lidocaine over a layer of viscoelastic. Preferably after injection the shoulder is used to hold the eye in place while further procedures comprising a possible second incision are performed.

Figure 3:
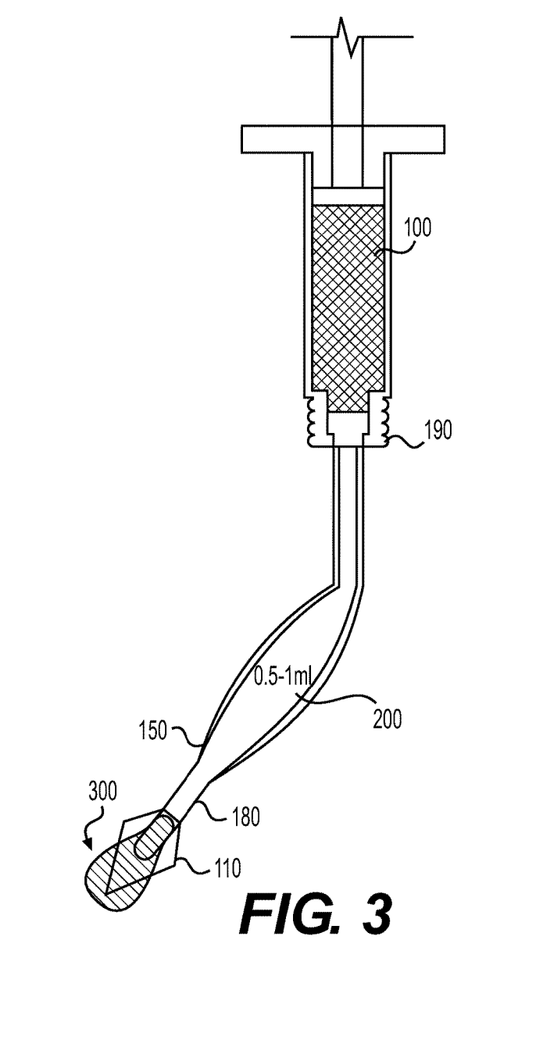
FIG. 3 illustrates a side view of a surgical cannulated blade according to a another embodiment.

In another embodiment illustrated in FIG. 3, the cannula includes a reservoir 200 to hold the lidocaine. This would eliminate the need to eject some viscoelastic from the syringe 110 and insert lidocaine into the space formed thereby, prior to attaching the syringe 100 to the blade. As illustrated in FIG. 3, the reservoir 200 is formed by a widening of the lumen 180 in the area of the shoulder forming the increasing diameter portion 150. In the embodiment, the reservoir 200 can hold approximately 0.5-1 ml of lidocaine.

Figure 4:
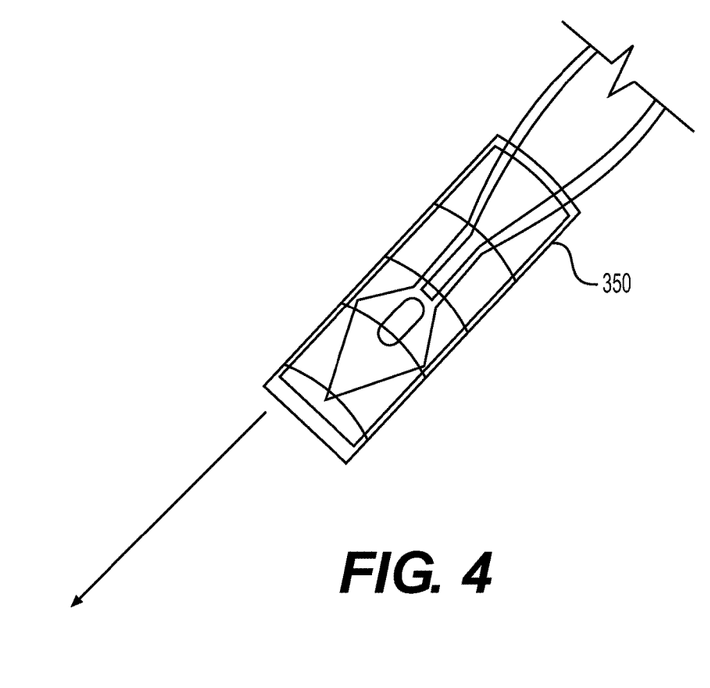
FIG. 4 illustrates a partial side view of a surgical cannulated blade according to a modification of the embodiment of FIG. 3.

In the embodiment, the lidocaine can be charged into the reservoir 200 at the threaded connection 190 prior to attachment of the syringe 100 thereto. To keep the lidocaine from escaping the opening of the lumen 180, a removable cap 300 covering the opening can be provided. Furthermore, in the modification illustrated in FIG. 4, the cap 350 can be configured to also protect the blade, and can snap-fit onto the shoulder. The arrow in that figure indicates the removal direction of the cap 350.

Figure 5:
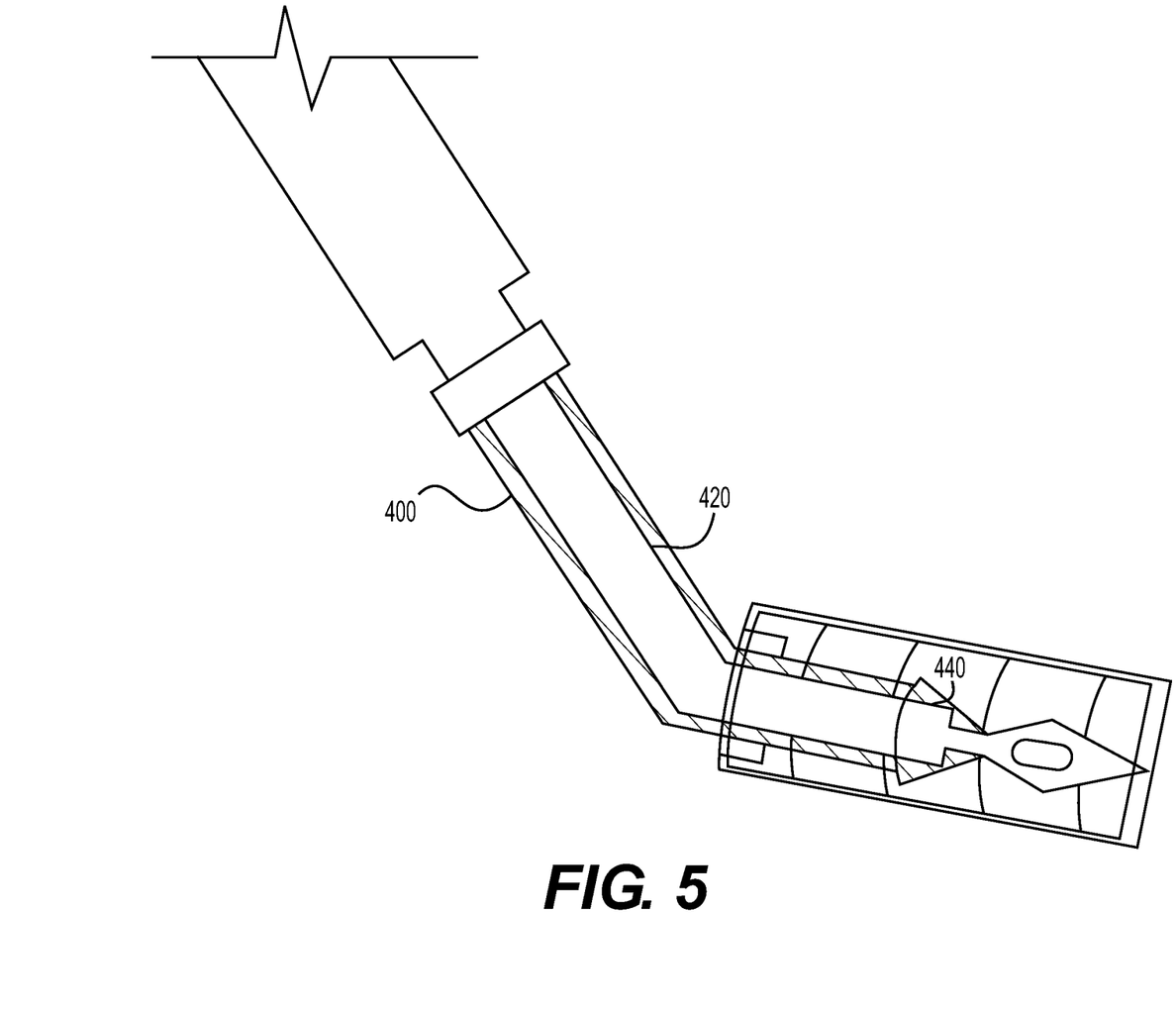
FIG. 5 illustrates a side view of a surgical cannulated blade according to a another embodiment.

FIG. 5 illustrates another blade with a cannula including a reservoir. However, unlike in the FIG. 4 embodiment, in which the reservoir is a hollowed out area of the device, the reservoir 400 in the FIG. 5 embodiment is provided by using a wider gauge cannula 420 at the top (for example, 10-15 gauge) in order to have sufficient space to fill the lidocaine, which then transitions down to a smaller gauge cannula 440 (for example, 25-27 gauge).

Figure 6:
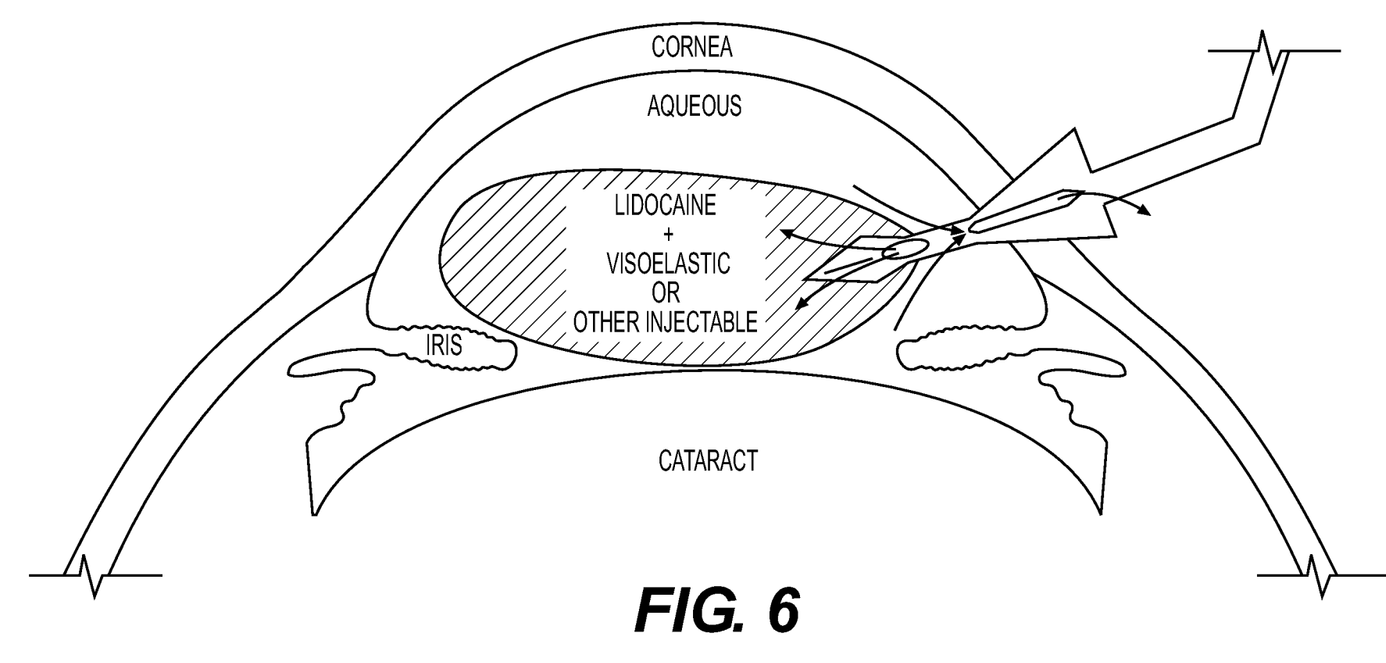
FIG. 6 illustrates a first step of a method of using the surgical cannulated blade.
Figure 7:
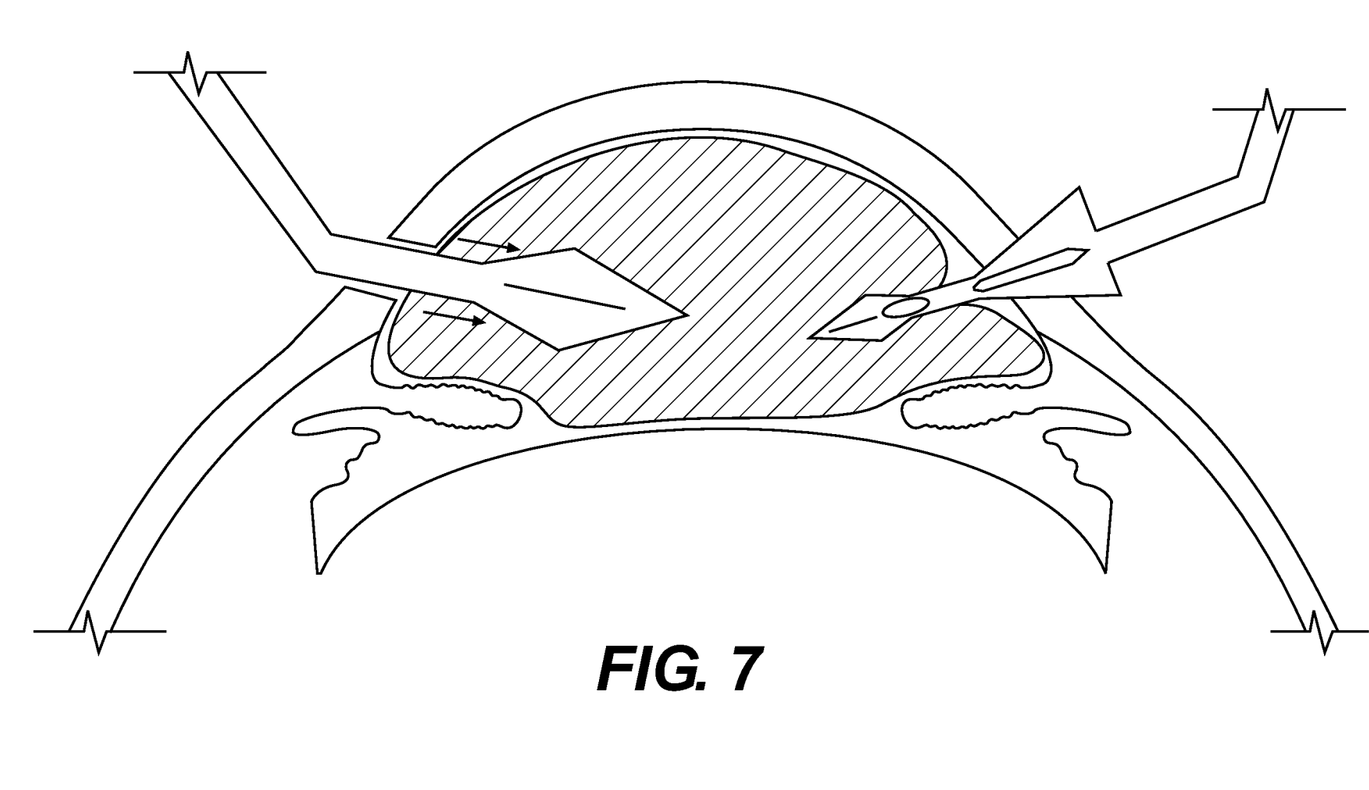
FIG. 7 illustrates a second step of a method of using the surgical cannulated blade.

FIG. 6 illustrates a first step of using the blade in a procedure involving the eye. In the step, the blade is used to create an opening in the cornea which is sealed and stabilized by inserting the shoulder into the opening. The lidocaine and viscoelastic are injected, and the indent functions as a vent allowing for egress of aqueous fluid. The indent is sized such that aqueous fluid can pass, but not the viscoelastic material. While the cannulated blade instrument is kept in position such that the shoulder maintains the sealing and stabilizing function, a main incision can then be created by a main blade as illustrated in FIG. 7, and a procedure then performed through the main incision.

Figure 8:
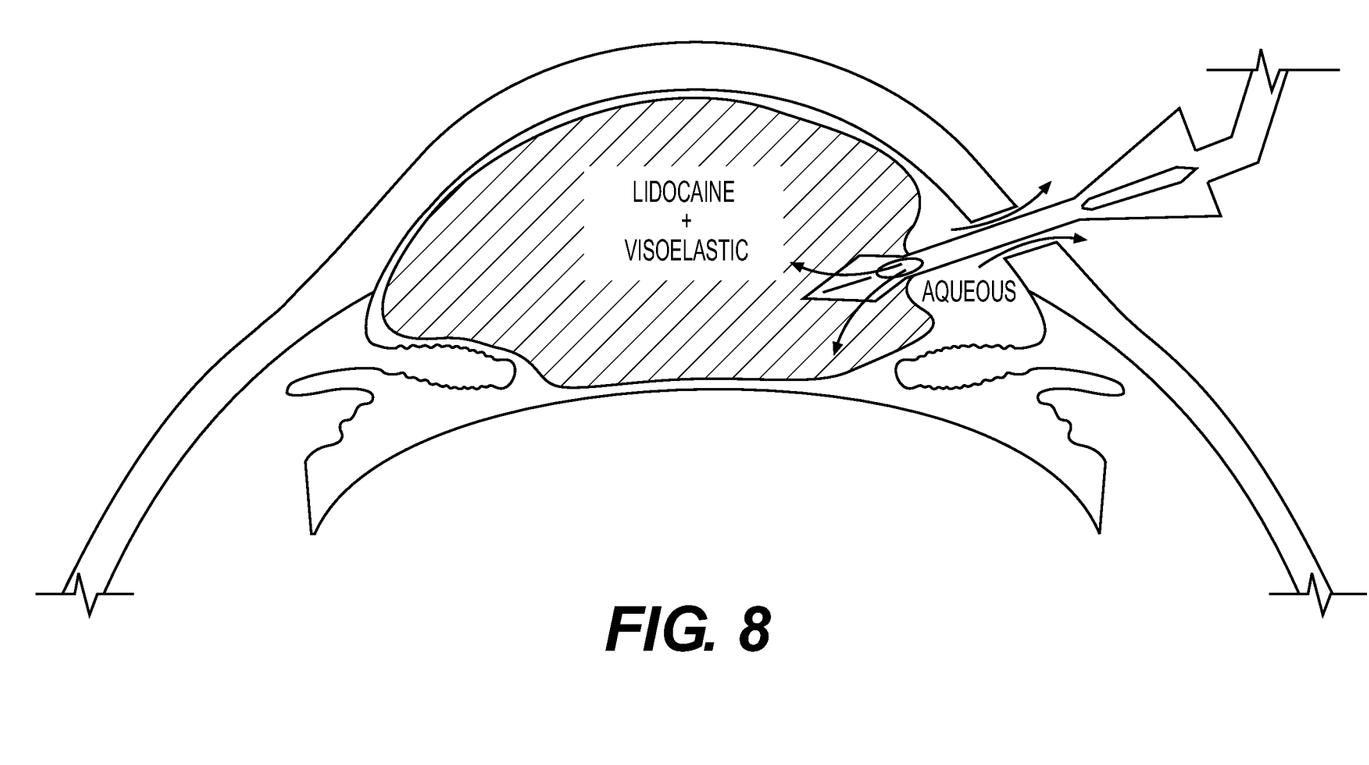
FIG. 8 illustrates a first step of a modified method using a modification of the surgical cannulated blade.
Figure 9:
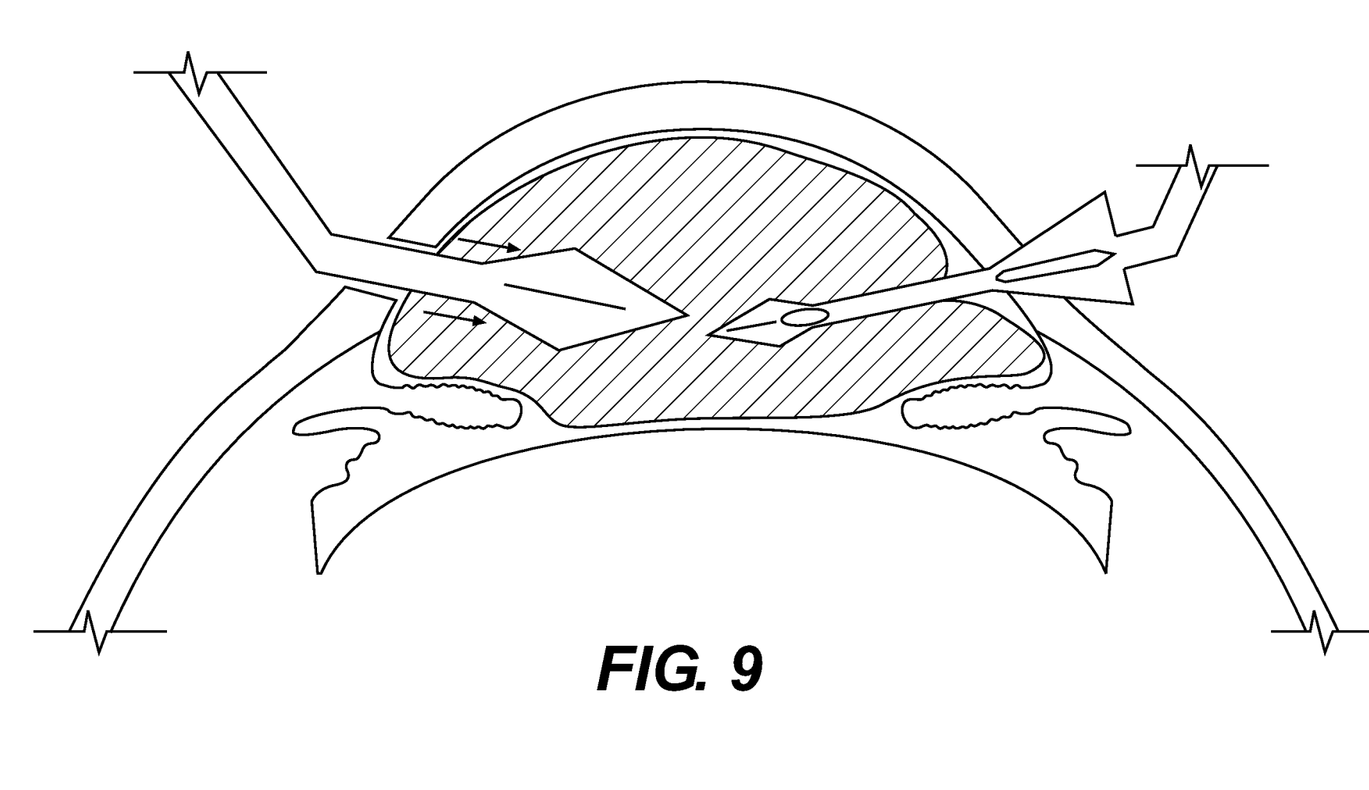
FIG. 9 illustrates a second step of a modified method using a modification of the surgical cannulated blade.

FIGS. 8 and 9 illustrate a modification in which the device includes a longer distance between the blade and the shoulder to allow the injectable to be placed further into the anterior chamber, and in which the shoulder is not placed in sealing position until after the injection. In this embodiment, the viscoelastic is less likely to reach the area of the opening formed by the instrument, and so sealing is not needed during injection, and aqueous egress can instead occur around the narrow portion of the cannula, and the indent in the shoulder is not needed when the instrument is used this way.

Embodiments of the invention have been disclosed in the forgoing specification. It is thus understood by those skilled in the art that many modifications and other embodiments of the invention will come to mind to which the invention pertains. It is thus understood that the invention is not limited to the specific embodiments disclosed herein, and that many modifications and other embodiments are intended to be included within the scope of the appended claims. Moreover, although specific terms are employed herein, as well as in the claims which follow, they are used only in a generic and descriptive sense, and not for the purpose of limiting the described invention, nor the claims which follow.

The invention claimed is:

1. A surgical cannulated blade instrument, comprising:
  a blade portion having a pointed end, a top surface, and a bottom surface opposite the top surface;
  an increasing diameter portion having a diameter which increases in a direction away from the pointed end; and
  a cannula portion having a lumen which opens at a location distal of the increasing diameter portion,
  wherein a distance between the pointed end and the increasing diameter portion is set such that, when the pointed end is disposed in an interior of a human eye, the increasing diameter portion can engage an opening in a cornea of the human eye, and
  wherein a length of the increasing diameter portion is set such that, when the increasing diameter portion engages the opening, the opening increases in diameter from an interior side of the opening to an exterior side of the opening.

2. The surgical cannulated blade instrument of claim 1, further comprising at least one indent in the increasing diameter portion.

3. The surgical cannulated blade instrument of claim 1, wherein the blade portion is upwardly curved to at least partially surround the cannula portion.

4. The surgical cannulated blade instrument of claim 1, further comprising a handle having a lumen in fluid communication with the lumen of the cannula portion.

5. The surgical cannulated blade instrument of claim 1, further comprising a reservoir containing anesthetic at a widened portion of the lumen within the increasing diameter portion.

6. The surgical cannulated blade instrument of claim 5, further comprising a removable cap covering the lumen opening to hold the anesthetic within the reservoir.

7. An eye surgery method comprising:
  incising a cornea of an eye using a blade portion of a surgical cannulated blade instrument according to claim 1 to create an opening in the cornea;
  injecting injectable into an anterior chamber of the eye through the opening by a lumen of the surgical cannulated blade; and
  stabilizing the eye by engaging an increasing diameter portion of the surgical cannulated blade with the opening.

8. A surgical cannulated instrument, comprising:
  an increasing diameter portion having a diameter which increases in a direction away from a distal end of the instrument,
  a cannula portion having a lumen which opens at a location distal of the increasing diameter portion, and
  at least one indent in the increasing diameter portion,
  wherein a distance between the distal end and the increasing diameter portion is set such that, when the distal end is disposed in an interior of a human eye, the increasing diameter portion can engage an opening in a cornea of the human eye, and
  wherein a length of the increasing diameter portion is set such that, when the increasing diameter portion engages the opening, the opening increases in diameter from an interior side of the opening to an exterior side of the opening.

9. The surgical cannulated instrument of claim 8, further comprising a handle having a lumen in fluid communication with the lumen of the cannula portion.

10. The surgical cannulated instrument of claim 8, further comprising a reservoir containing anesthetic at a widened portion of the lumen within the increasing diameter portion.

11. The surgical cannulated instrument of claim 10, further comprising a removable cap covering the lumen opening to hold the anesthetic within the reservoir.

\* \* \* \* \*